United States Patent
McConnell et al.

(10) Patent No.: US 10,671,701 B2
(45) Date of Patent: Jun. 2, 2020

(54) RADIOLOGY DESKTOP INTERACTION AND BEHAVIOR FRAMEWORK

(71) Applicant: General Electric Company, Schenectady, NY (US)

(72) Inventors: Kristen Alane McConnell, Pittsburgh, PA (US); Gretchen Marie Mendoza, Pittsburgh, PA (US); Anna Louise Von Reden, Pittsburgh, PA (US); Bryon Pigg, Pittsburgh, PA (US); Francesco DeSensi, Pittsburgh, PA (US); Gregory Hopkins, Pittsburgh, PA (US); Michael Butler, Pittsburgh, PA (US); Xiaoyu Chen Kaess, Pittsburgh, PA (US); Rasu Shrestha, Pittsburgh, PA (US)

(73) Assignee: General Electric Company, Schenectady, NY (US)

( * ) Notice: Subject to any disclaimer, the term of this patent is extended or adjusted under 35 U.S.C. 154(b) by 703 days.

(21) Appl. No.: 14/554,637

(22) Filed: Nov. 26, 2014

(65) Prior Publication Data
US 2016/0147938 A1    May 26, 2016

(51) Int. Cl.
| | | |
|---|---|---|
| *G06F 19/00* | (2018.01) | |
| *G06F 3/0482* | (2013.01) | |
| *G16H 10/60* | (2018.01) | |

(52) U.S. Cl.
CPC .......... *G06F 19/321* (2013.01); *G06F 3/0482* (2013.01); *G06F 19/34* (2013.01); *G16H 10/60* (2018.01)

(58) Field of Classification Search
CPC ....... G06F 19/321; G06F 19/34; G06F 3/0482
See application file for complete search history.

(56) References Cited

U.S. PATENT DOCUMENTS 5,633,910 A * 5/1997 Cohen .................... A61B 5/117
                                                            379/38
2002/0133373 A1* 9/2002 Silva-Craig ........... G06F 19/321
                                                            705/2

(Continued)

OTHER PUBLICATIONS

Bui, Alex "openSourcePACS: An Extensible Infrastructure for Medical Image Management" Jan. 2007, IEEE Transactions on Information Technology in Biomedicine vol. 11. (Year: 2007).*

*Primary Examiner* — Manglesh M Patel
*Assistant Examiner* — Nicholas Hasty
(74) *Attorney, Agent, or Firm* — Hanley, Flight and Zimmerman, LLC

(57) ABSTRACT

Disclosed and described systems, methods, and apparatus provide diagnostic display and analysis of patient data. An example radiology desktop system includes a workload manager that organizes and displays one or more worklists. The example workload manager retrieves and displays, based on receiving a selection of an active worklist, one or more exams associated with the active worklist. The example system includes a diagnostic hub triggered based on selection of an exam. The example diagnostic hub generates an exam preview panel provides a summary of the selected exam. The example diagnostic hub facilitates comparison, based on selection of a comparison exam via the user interface from a patient library, between the selected exam and the comparison exam via the diagnostic hub. The example diagnostic hub updates a worklist entry for the selected exam based on an analysis resulting from the comparison between the selected exam and the comparison exam.

17 Claims, 14 Drawing Sheets

(56) References Cited

U.S. PATENT DOCUMENTS

| | | | |
|---|---|---|---|
| 2007/0143150 A1* | 6/2007 | Sasai | G06F 19/3487 705/3 |
| 2007/0198250 A1* | 8/2007 | Mardini | G06F 17/243 704/9 |
| 2009/0287500 A1* | 11/2009 | Benjamin | G06F 19/321 705/2 |
| 2010/0131292 A1* | 5/2010 | Hawkins | G06Q 10/06 705/3 |
| 2011/0198702 A1* | 8/2011 | Ohmi | H01L 21/28079 257/369 |
| 2011/0209078 A1* | 8/2011 | Pearson | G06F 3/0481 715/767 |
| 2011/0219321 A1* | 9/2011 | Gonzalez Veron | G06F 3/048 715/764 |

* cited by examiner

RADIOLOGY DESKTOP INTERACTION AND BEHAVIOR FRAMEWORK

FIELD OF DISCLOSURE

The present disclosure relates to clinical workflow interaction framework, and more particularly to systems, methods and computer program products to facilitate dynamic workflow management, interaction, and adaptive interface composition via a diagnostic hub.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

BRIEF SUMMARY

In view of the above, there is a need for systems, methods, and computer program products which facilitate diagnostic display and analysis of patient data. The above-mentioned needs are addressed by the subject matter described herein and will be understood in the following specification.

Certain examples provide a method to facilitate diagnostic display and analysis of patient data. The example method includes triggering, based on a user identification, activation of a workload manager. The example workload manager organizes and displays, via a user interface on a display, one or more worklists associated with the user identification, and the workload manager adjusts a configuration of the display to display the one or more worklists. The example method also includes retrieving and displaying, based on receiving a selection of an active worklist from the one or more worklists displayed via the workload manager, one or more exams associated with the active worklist. The example workload manager adjusts the configuration of the display to display the active worklist and the one or more exams associated with the active worklist. The example method further includes triggering, based on selection of an exam from the one or more exams, activation of a diagnostic hub. The example diagnostic hub organizes and displays, via the user interface on the display, a diagnostic view of information for the selected exam and a patient associated with the selected exam. The example method includes generating, via the diagnostic hub, an exam preview panel providing a summary of the selected exam. The example diagnostic hub adjusts the configuration of the display to display the exam preview panel in conjunction with the selected exam and the active worklist. The example method includes facilitating comparison, based on selection of a comparison exam via the user interface from a patient library, between the selected exam and the comparison exam via the diagnostic hub. The example diagnostic hub adjusts the configuration of the display for the comparison. The example method includes updating a worklist entry for the selected exam based on an analysis resulting from the comparison between the selected exam and the comparison exam.

Certain examples provide a radiology desktop system. The example system includes a processor configured to implement a user interface displaying information on a display. The example processor is also configured to implement a workload manager triggered based on a user identification. The example workload manager organizes and displays, via the user interface on the display, one or more worklists associated with the user identification. The example workload manager adjusts a configuration of the display to display the one or more worklists. The example workload manager retrieves and displays, based on receiving a selection of an active worklist from the one or more worklists displayed via the workload manager, one or more exams associated with the active worklist. The example workload manager adjusts the configuration of the display to display the active worklist and the one or more exams associated with the active worklist. The example processor is further configured to implement a diagnostic hub triggered based on selection of an exam from the one or more exams. The example diagnostic hub organizes and displays, via the user interface on the display, a diagnostic view of information for the selected exam and a patient associated with the selected exam. The example diagnostic hub generates an exam preview panel providing a summary of the selected exam. The example diagnostic hub adjusts the configuration of the display to display the exam preview panel in conjunction with the selected exam and the active worklist. The example diagnostic hub facilitates comparison, based on selection of a comparison exam via the user interface from a patient library, between the selected exam and the comparison exam via the diagnostic hub. The example diagnostic hub adjusts the configuration of the display for the comparison. The example diagnostic hub updates a worklist entry for the selected exam based on an analysis resulting from the comparison between the selected exam and the comparison exam.

Certain examples provide a computer-readable storage medium including program instructions for execution by a computing device. The instructions, when executed, causing the computing device to implement a radiology desktop system. The example system includes a user interface displaying information on a display. The example system includes a workload manager triggered based on a user identification. The example workload manager organizes and displays, via the user interface on the display, one or more worklists associated with the user identification. The example workload manager adjusts a configuration of the display to display the one or more worklists. The example workload manager retrieves and displays, based on receiving a selection of an active worklist from the one or more worklists displayed via the workload manager, one or more exams associated with the active worklist. The example workload manager adjusts the configuration of the display to display the active worklist and the one or more exams associated with the active worklist. The example system includes a diagnostic hub triggered based on selection of an exam from the one or more exams. The example diagnostic hub organizes and displays, via the user interface on the display, a diagnostic view of information for the selected exam and a patient associated with the selected exam. The example diagnostic hub generates an exam preview panel provides a summary of the selected exam. The example diagnostic hub adjusts the configuration of the display to display the exam preview panel in conjunction with the selected exam and the active worklist. The example diagnostic hub facilitates comparison, based on selection of a comparison exam via the user interface from a patient library, between the selected exam and the comparison exam via the diagnostic hub. The example diagnostic hub adjusts the configuration of the display for the comparison. The example diagnostic hub updates a worklist entry for the selected exam based on an analysis resulting from the comparison between the selected exam and the comparison exam.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

Figure 1:
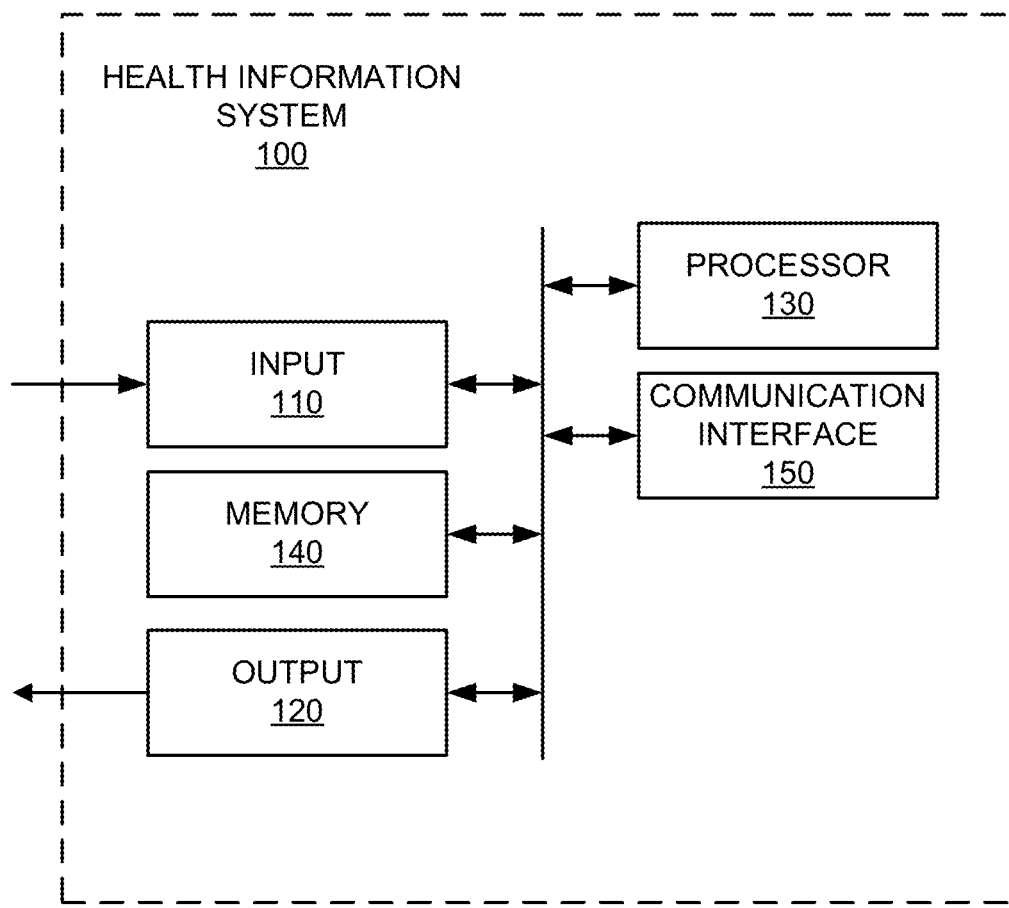
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. OVERVIEW

Aspects disclosed and described herein enable a radiology desktop facilitating a radiology workflow. An example radiology desktop provides an interaction framework in which a worklist is integrated with a diagnostic space and can be manipulated into and out of the diagnostic space to progress from a daily worklist to a particular diagnosis/diagnostic view for a patient (and back to the daily worklist). The radiology desktop shows the radiologist what is to be done and on what task(s) the radiologist is current working.

In certain examples, the radiology desktop provides a diagnostic hub and facilitates a dynamic workflow and adaptive composition of a graphical user interface. For example, the radiology desktop provides an intelligently adaptive, dynamically adjustable interface based on information, not just user clicks, as well as dynamic real time updates from a server. The radiology desktop provides a higher level framework built with multiple roles in mind (e.g., not only radiology but other -ologies as well to unify workflows and provide an expandable and reusable framework). Additionally, areas of the radiology desktop interact such that an action on one client and triggers notification of another client regarding state change(s) corresponding to the action.

In an example, one side (e.g., a left hand side) of the radiologist desktop is configurable by the radiologist. The radiologist can select a worklist on the left side of the desktop graphical user interface (GUI), and the worklist appears (e.g., "pops out" or is otherwise displayed) on the side of the radiologist desktop GUI.

Certain examples provide a radiology desktop ("Rad Desktop") that combines features for a radiologist's workflow into a single application. These features include: workload management, case selection, and access to relevant prior documentation via a patient library. A visual hierarchy supports consolidation of functionality by arranging data into compact zones that can be scanned quickly, for example.

In certain examples, the visual hierarchy of the radiology desktop supports an underlying functional framework by providing clarity to workflow elements. In certain examples, visual paradigms such as a Worklist Counter, Item Display, Clinical Journey, and My Comparisons are arranged in a very deliberate fashion. These arrangements are the product of months of design iteration, user research, and validation, for example. The visual hierarchy of the radiology desktop collects appropriate data for each element of a radiologist's workflow into a concise presentation. The radiology desktop eliminates a need for multiple applications and monitors to display non-imaging elements of the radiology workflow, for example.

Other aspects, such as those discussed in the following and others as can be appreciated by one having ordinary skill in the art upon reading the enclosed description, are also possible.

II. EXAMPLE OPERATING ENVIRONMENT

Health information, also referred to as healthcare information and/or healthcare data, relates to information generated and/or used by a healthcare entity. Health information can be information associated with health of one or more patients, for example. Health information can include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure can include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

a. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. The example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of the example system 100 can be integrated in one device or distributed over two or more devices.

The example input 110 can include a keyboard, a touch-screen, a mouse, a trackball, a track pad, optical barcode recognition, voice command, etc. or combination thereof used to communicate an instruction or data to the system 100. The example input 110 can include an interface between systems, between user(s) and the system 100, etc.

The example output 120 can provide a display generated by the processor 130 for visual illustration on a monitor or the like. The display can be in the form of a network interface or graphic user interface (GUI) to exchange data, instructions, or illustrations on a computing device via the communication interface 150, for example. The example output 120 can include a monitor (e.g., liquid crystal display (LCD), plasma display, cathode ray tube (CRT), etc.), light emitting diodes (LEDs), a touch-screen, a printer, a speaker, or other conventional display device or combination thereof.

The example processor 130 includes hardware and/or software configuring the hardware to execute one or more tasks and/or implement a particular system configuration. The example processor 130 processes data received at the input 110 and generates a result that can be provided to one or more of the output 120, memory 140, and communication interface 150. For example, the example processor 130 can take user annotation provided via the input 110 with respect to an image displayed via the output 120 and can generate a report associated with the image based on the annotation. As another example, the processor 130 can process updated patient information obtained via the input 110 to provide an updated patient record to an EMR via the communication interface 150.

The example memory 140 can include a relational database, an object-oriented database, a data dictionary, a clinical data repository, a data warehouse, a data mart, a vendor neutral archive, an enterprise archive, etc. The example memory 140 stores images, patient data, best practices, clinical knowledge, analytics, reports, etc. The example memory 140 can store data and/or instructions for access by the processor 130. In certain examples, the memory 140 can be accessible by an external system via the communication interface 150.

In certain examples, the memory 140 stores and controls access to encrypted information, such as patient records, encrypted update-transactions for patient medical records, including usage history, etc. In an example, medical records can be stored without using logic structures specific to medical records. In such a manner the memory 140 is not searchable. For example, a patient's data can be encrypted with a unique patient-owned key at the source of the data. The data is then uploaded to the memory 140. The memory 140 does not process or store unencrypted data thus minimizing privacy concerns. The patient's data can be downloaded and decrypted locally with the encryption key.

For example, the memory 140 can be structured according to provider, patient, patient/provider association, and document. Provider information can include, for example, an identifier, a name, and address, a public key, and one or more security categories. Patient information can include, for example, an identifier, a password hash, and an encrypted email address. Patient/provider association information can include a provider identifier, a patient identifier, an encrypted key, and one or more override security categories. Document information can include an identifier, a patient identifier, a clinic identifier, a security category, and encrypted data, for example.

The example communication interface 150 facilitates transmission of electronic data within and/or among one or more systems. Communication via the communication interface 150 can be implemented using one or more protocols. In some examples, communication via the communication interface 150 occurs according to one or more standards (e.g., Digital Imaging and Communications in Medicine (DICOM), Health Level Seven (HL7), ANSI X12N, etc.). The example communication interface 150 can be a wired interface (e.g., a data bus, a Universal Serial Bus (USB) connection, etc.) and/or a wireless interface (e.g., radio frequency, infrared, near field communication (NFC), etc.). For example, the communication interface 150 can communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

b. Example Healthcare Infrastructure

Figure 2:
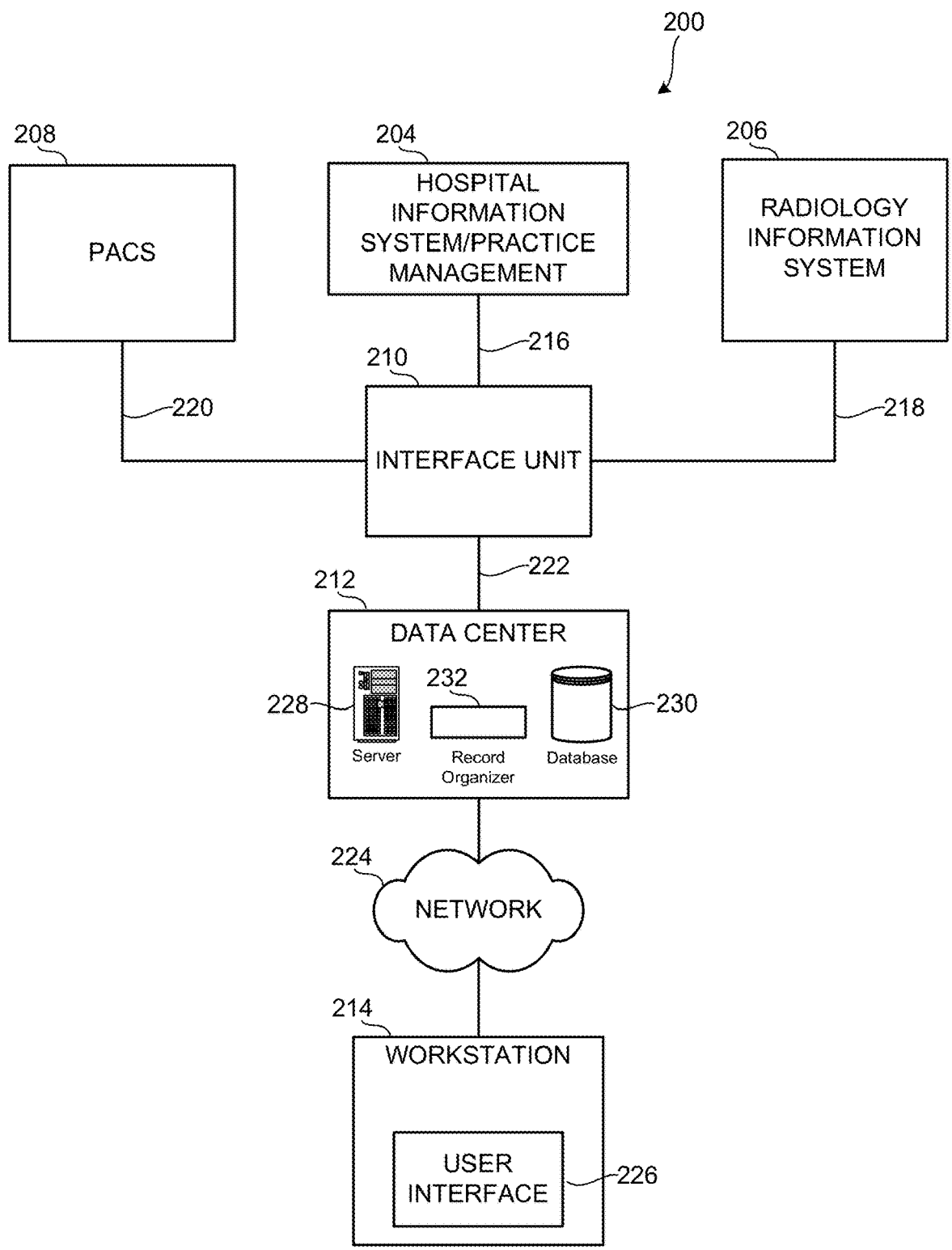
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. The example healthcare system 200 includes a HIS 204, a RIS 206, a PACS 208, an interface unit 210, a data center 212, and a workstation 214. In the illustrated example, the HIS 204, the RIS 206, and the PACS 208 are housed in a healthcare facility and locally archived. However, in other implementations, the HIS 204, the RIS 206, and/or the PACS 208 can be housed one or more other suitable locations. In certain implementations, one or more of the PACS 208, RIS 206, HIS 204, etc., can be implemented remotely via a thin client and/or downloadable software solution. Furthermore, one or more components of the healthcare system 200 can be combined and/or implemented together. For example, the RIS 206 and/or the PACS 208 can be integrated with the HIS 204; the PACS 208 can be integrated with the RIS 206; and/or the three example information systems 204, 206, and/or 208 can be integrated together. In other example implementations, the healthcare system 200 includes a subset of the illustrated information systems 204, 206, and/or 208. For example, the healthcare system 200 can include only one or two of the HIS 204, the RIS 206, and/or the PACS 208. Information (e.g., scheduling, test results, exam image data, observations, diagnosis, etc.) can be entered into the HIS 204, the RIS 206, and/or the PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). The RIS 206 stores information such as, for example, radiology reports, radiology exam image data, messages, warnings, alerts, patient scheduling information, patient demographic data, patient tracking information, and/or physician and patient status monitors. Additionally, the RIS 206 enables exam order entry (e.g., ordering an x-ray of a patient) and image and film tracking (e.g., tracking identities of one or more people that have checked out a film). In some examples, information in the RIS 206 is formatted according to the HL-7 (Health Level Seven) clinical communication protocol. In certain examples, a medical exam distributor is located in the RIS 206 to facilitate distribution of radiology exams to a radiologist workload for review and management of the exam distribution by, for example, an administrator.

The PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine (DICOM) format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

The interface unit 210 includes a hospital information system interface connection 216, a radiology information system interface connection 218, a PACS interface connection 220, and a data center interface connection 222. The interface unit 210 facilities communication among the HIS 204, the RIS 206, the PACS 208, and/or the data center 212. The interface connections 216, 218, 220, and 222 can be implemented by, for example, a Wide Area Network (WAN) such as a private network or the Internet. Accordingly, the interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

The interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 214 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 214 receives commands and/or other input from a user via, for example, a keyboard, mouse, track ball, microphone, etc. The workstation 214 is capable of implementing a user interface 226 to enable a healthcare practitioner and/or administrator to interact with the healthcare system 200. For example, in response to a request from a physician, the user interface 226 presents a patient medical history. In other examples, a radiologist is able to retrieve and manage a workload of exams distributed for review to the radiologist via the user interface 226. In further examples, an administrator reviews radiologist workloads, exam allocation, and/or operational statistics associated with the distribution of exams via the user interface 226. In some examples, the administrator adjusts one or more settings or outcomes via the user interface 226.

The example data center 212 of FIG. 2 is an archive to store information such as images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider (ASP) and is located in a centralized location that can be accessed by a plurality of systems and facilities (e.g., hospitals, clinics, doctor's offices, other medical offices, and/or terminals). In some examples, the data center 212 can be spatially distant from the HIS 204, the RIS 206, and/or the PACS 208 (e.g., at GENERAL ELECTRIC® headquarters).

The example data center 212 of FIG. 2 includes a server 228, a database 230, and a record organizer 232. The server 228 receives, processes, and conveys information to and from the components of the healthcare system 200. The database 230 stores the medical information described herein and provides access thereto. The example record organizer 232 of FIG. 2 manages patient medical histories, for example. The record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by the system 200 via a software-as-a-service (SaaS) implementation over a cloud or other computer network, for example. In certain examples, all or part of the system 200 can also be provided via platform as a service (PaaS), infrastructure as a service (IaaS), etc. For example, the system 200 can be implemented as a cloud-delivered Mobile Computing Integration Platform as a Service. A set of consumer-facing Web-based, mobile, and/or other applications enable users to interact with the PaaS, for example.

c. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, provide a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
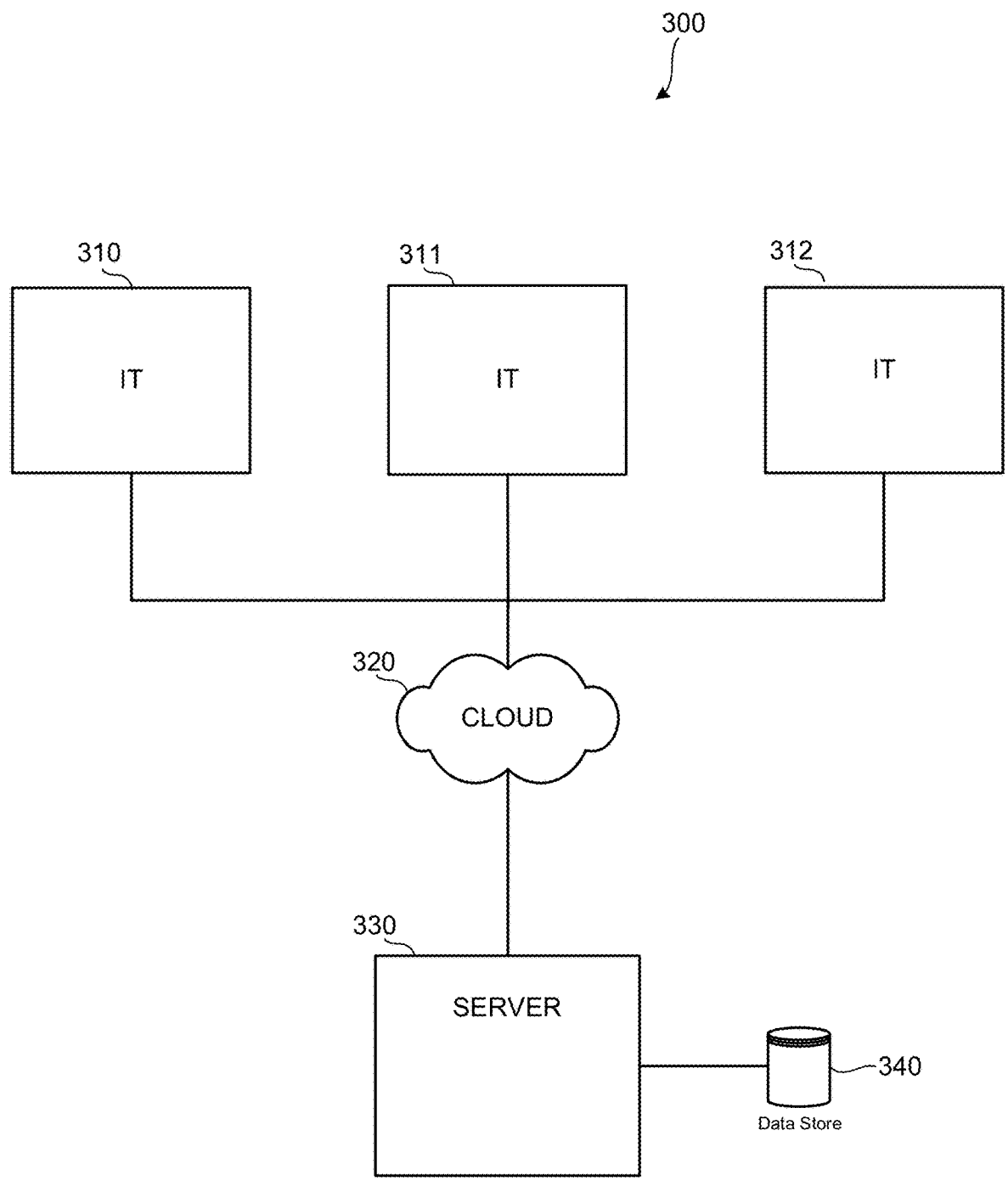
FIG. 3 shows an example industrial internet configuration including a plurality of health-focused systems.

FIG. 3 illustrates an example industrial internet configuration 300. The example configuration 300 includes a plurality of health-focused systems 310-312, such as a plurality of health information systems 100 (e.g., PACS, RIS, EMR, etc.) communicating via the industrial internet infrastructure 300. The example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 in the system 300 become "intelligent" as a network with advanced sensors, controls, and software applications. Using such an infrastructure, advanced analytics can be provided to associated data. The analytics combines physics-based analytics, predictive algorithms, automation, and deep domain expertise. Via the cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

d. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

e. Example Methods of Use

Clinical workflows are typically defined to include one or more steps, elements, and/or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions, elements, and/or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows can include manual actions, elements, and/or steps to be taken by, for example, an administrator or practitioner, electronic actions, elements, and/or steps to be taken by a system or device, and/or a combination of manual and electronic action(s), element(s), and/or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

For example, a radiology department in a hospital, clinic, or other healthcare facility facilitates a sequence of events for patient care of a plurality of patients. At registration and scheduling, a variety of information is gathered such as patient demographic, insurance information, etc. The patient can be registered for a radiology procedure, and the procedure can be scheduled on an imaging modality.

Before the patient arrives for the scheduled procedures, pre-imaging activities can be coordinated. For example, the patient can be advised on pre-procedure dietary restrictions, etc. Upon arrive, the patient is checked-in, and patient information is verified. Identification, such as a patient identification tag, etc., is issued.

Then, the patient is prepared for imaging. For example, a nurse or technologist can explain the imaging procedure, etc. For contrast media imaging, the patient is prepared with contrast media etc. The patient is guided through the imaging procedure, and image quality is verified. Using an image viewer and reporting tools, the radiologist reads the resulting image(s), performs dictation in association with the images, and approves associated reports. A billing specialist can prepare a claim for each completed procedure, and claims can be submitted to an insurer.

Such a workflow can be facilitated via an improved user desktop interface, for example.

III. EXAMPLE RADIOLOGY DESKTOP INTERFACE SYSTEMS

Certain examples provide a radiology desktop interface which combines workload management tools with a new, patient-centric exam reading space (referred to herein as a "Diagnostic Hub"). Exam data for one or more patients can be displayed via the diagnostic hub, which provides support for a radiologist's workflow.

Figure 4:
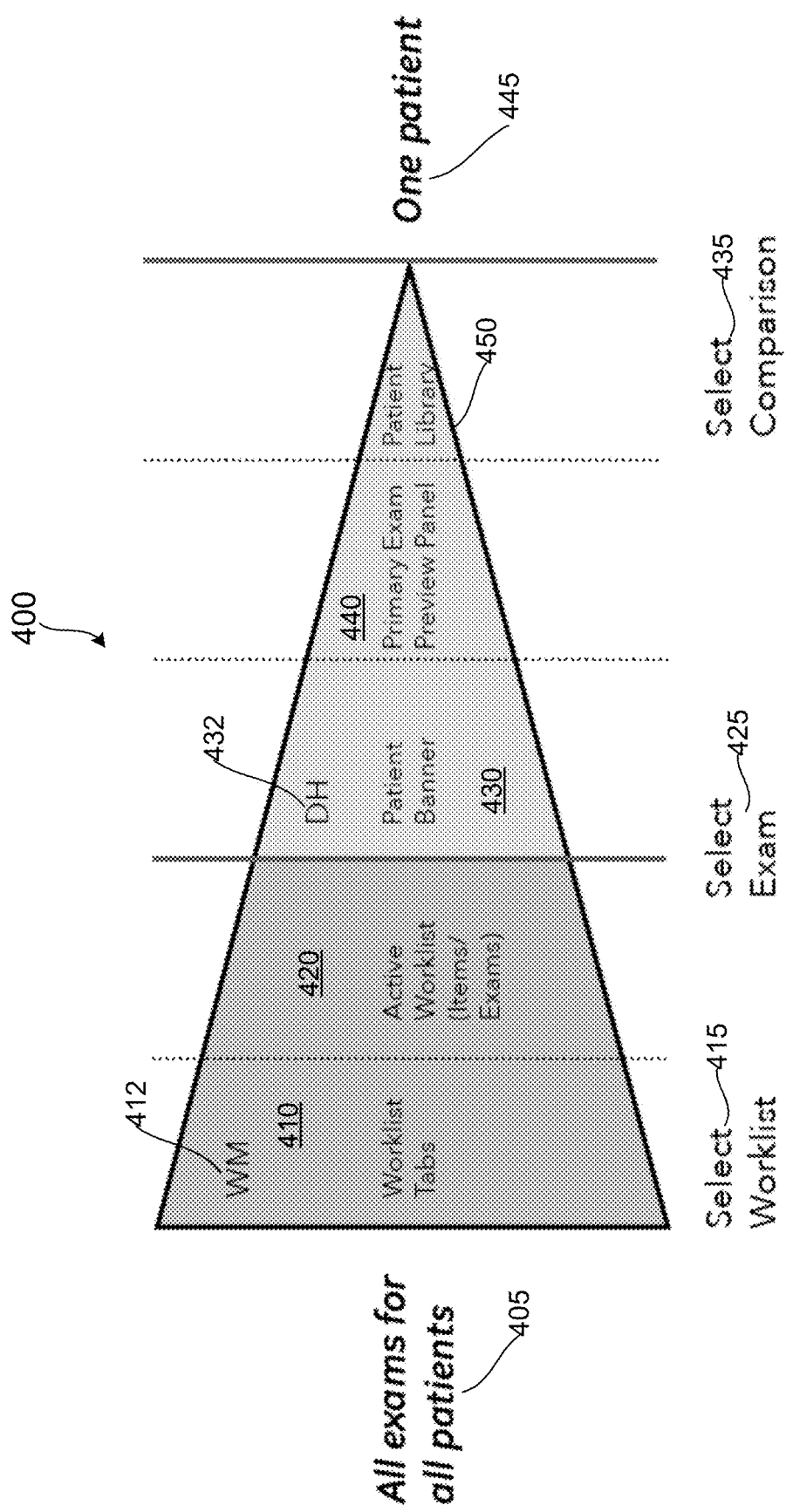
FIG. 4 illustrates an example of a left-to-right drill-down model.

Radiology desktop is design to support the radiologist workflow from a bird's eye view or overview of available unread exams to a nuts and bolts or detail view of a detailed clinical context for a single patient. FIG. 4 illustrates an example of a left-to-right drill-down model 400. The model flow 400 provides a framework for wayfinding as users move from macro to micro and back again. The model 400 continuously orients users in their current tasks.

As shown in the example of FIG. 4, exams for patients in a collection of patients (e.g., patients associated with a physician, patients in a department, patients in a hospital, etc.) 405 are provided to a workload manager 412 including worklist tabs 410. A worklist is selected 415 and an active worklist 420 is provided via the workload manager 412. The active worklist 420 displayed via the workload manager 412 includes exams and other items for the selected worklist. An exam can be selected 425 from the active worklist 420.

The selected exam 425 is provided via a diagnostic hub 432. The diagnostic hub 432 provides a patient banner 430 in conjunction with the selected exam 425. A primary exam preview panel 440 can be selected from the patient banner 430. Via the primary exam preview panel 440, a patient library 450 can be accessed. Using the patient library 450, a patient 445 can be selected for comparison 435.

Figure 5:
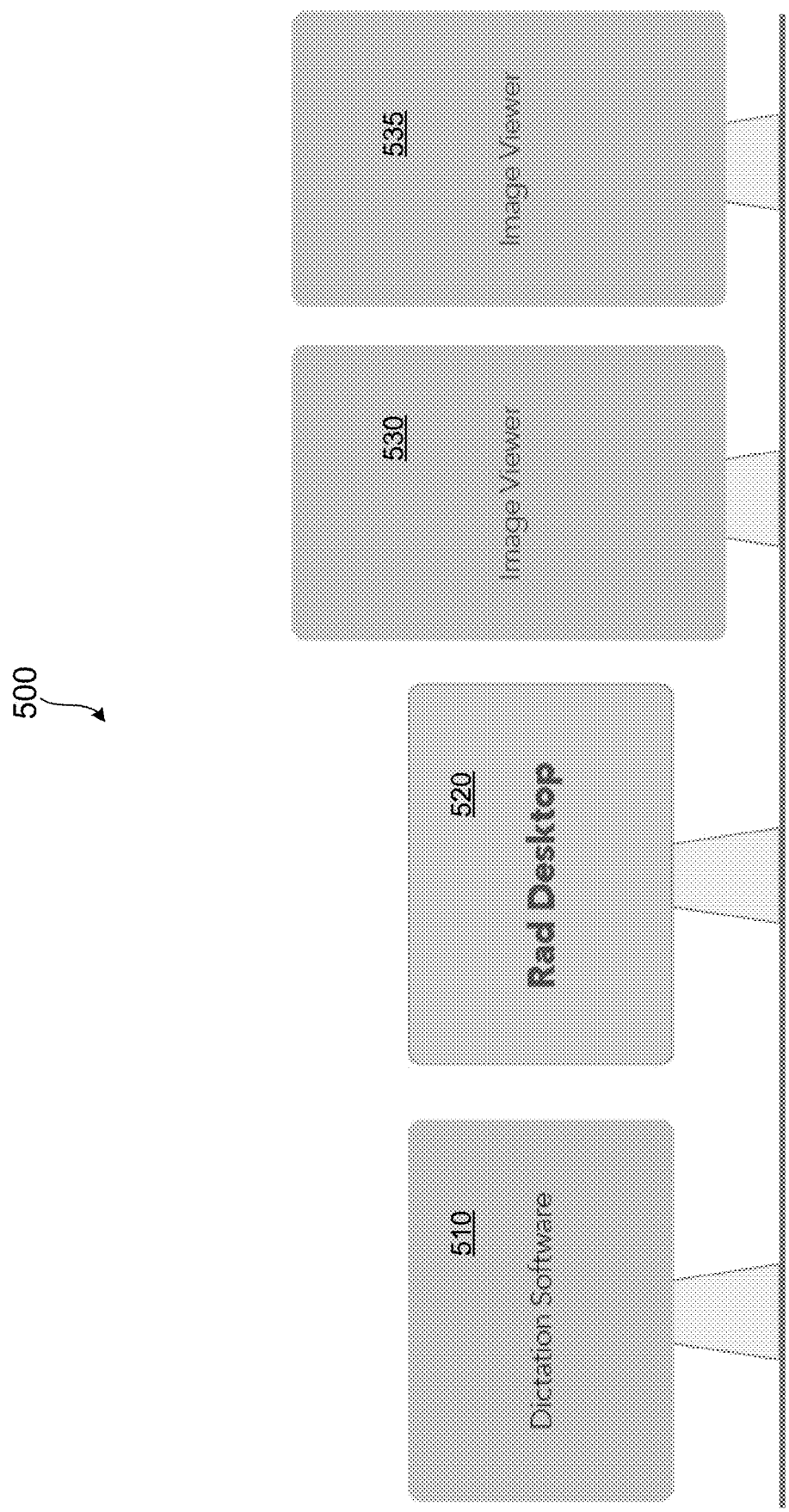
FIG. 5 illustrates an example image viewer implemented on a plurality of diagnostic monitors.

In certain examples, exam imaging can be handled by a separate viewer application while dictation and report management is provided by another application. As shown in the example of FIG. 5, an image viewer is implemented on a plurality of diagnostic monitors 530, 535. A dictation application 510 either sits side-by-side with a radiology desktop 520, on a same monitor as the radiology desktop 520, or behind/in front of the radiology desktop 520 such that a user toggles between two windows 510, 520. In other examples, image viewing, image analysis, and/or dictation can be combined on a single workstation.

In certain examples, a workload manager resides on a side (e.g., a left-hand side, a right-hand side, top, bottom, etc.) of a radiology desktop and can be opened or otherwise accessed to access exams. When an exam access is not desired, the workload manager can be closed or hidden with respect to the radiology desktop (e.g., with respect to a diagnostic hub on the radiology desktop).

Figure 6A:
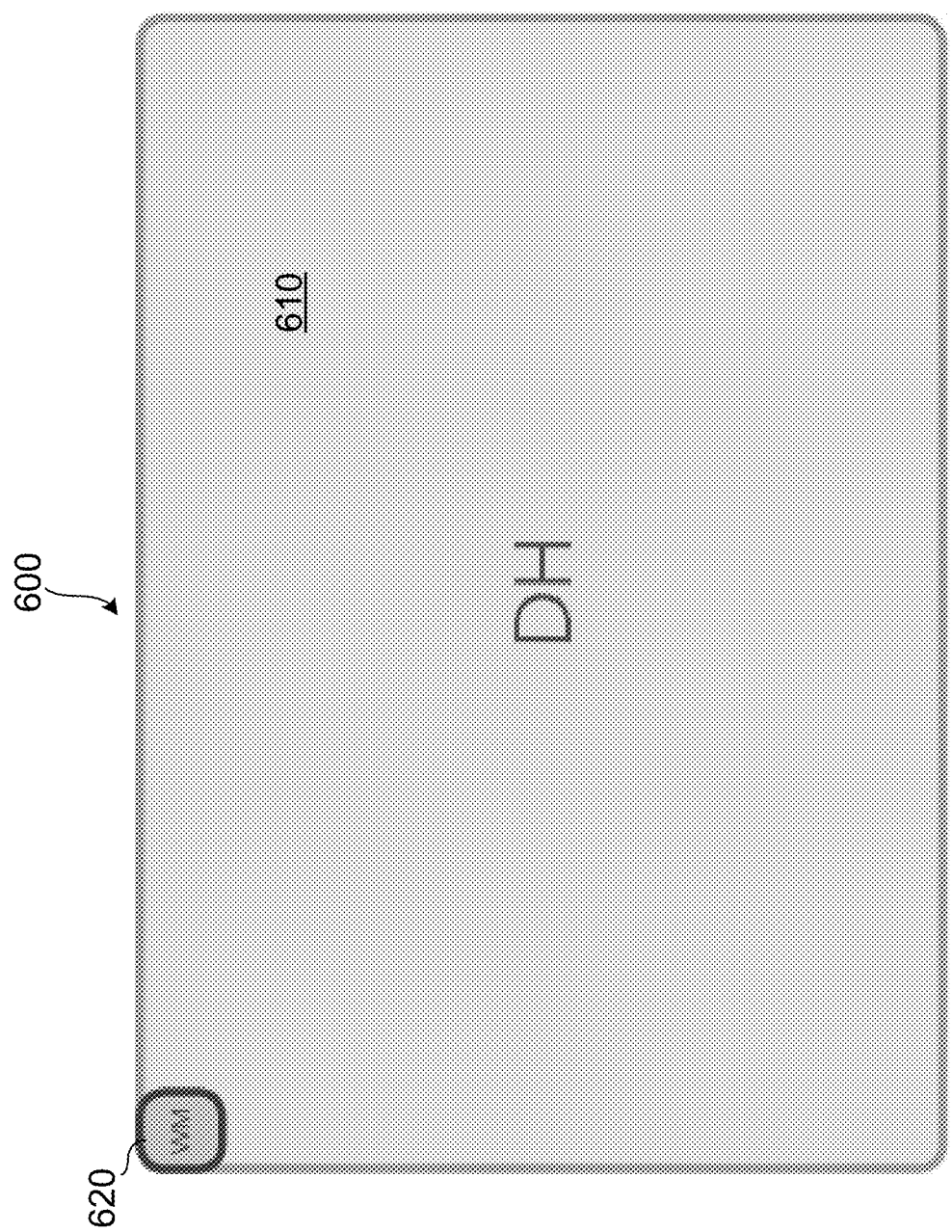
FIGS. 6A-6D illustrate a sequence or evolution of display configuration.
Figure 6B:
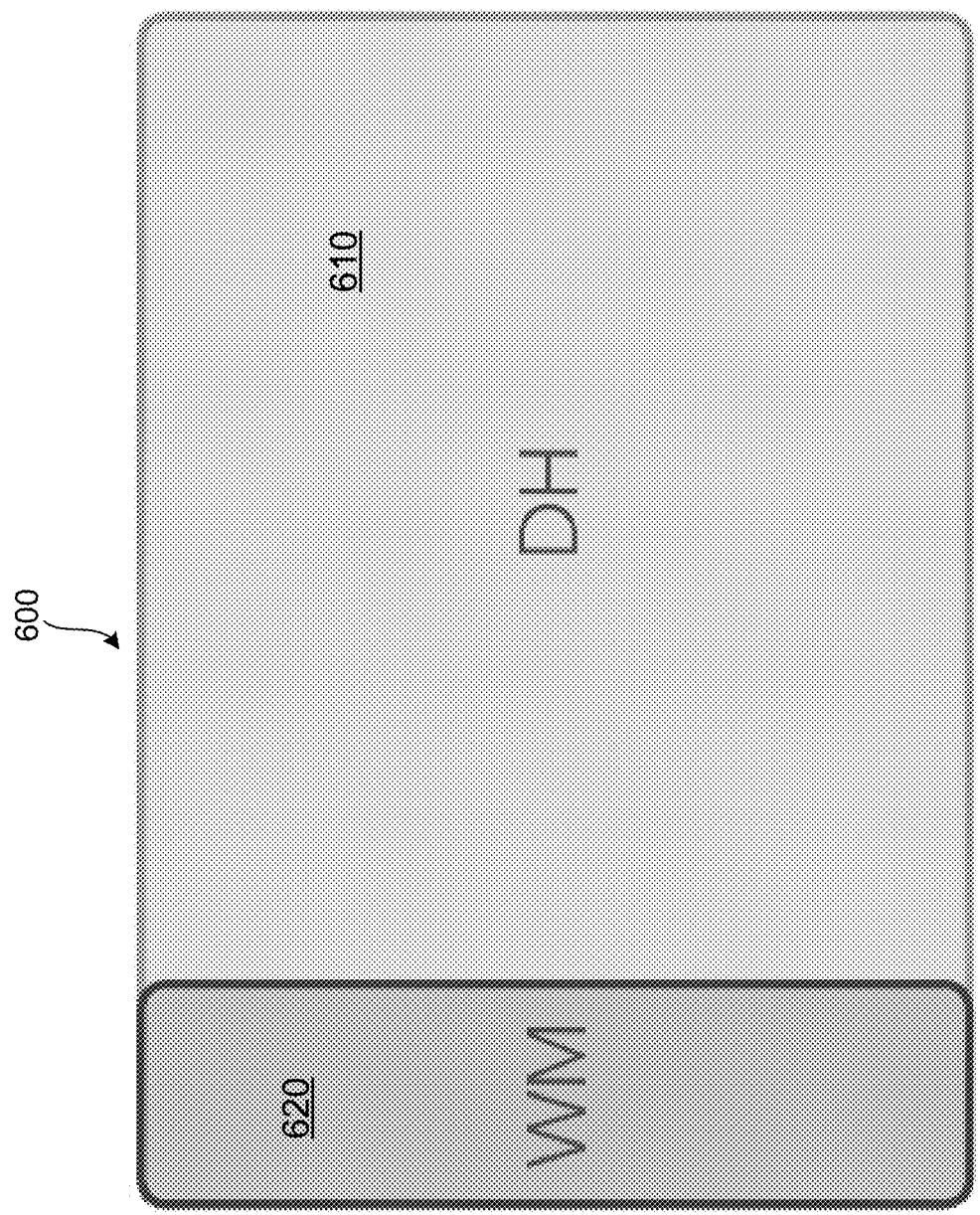

FIGS. 6A-6D illustrate a sequence or evolution of display configuration. As shown in the example of FIG. 6A, a diagnostic hub 610 occupies a majority of available display area on a display 600, and a workload manager 620 is represented in miniaturized or icon form. The workload manager 620 can be minimized where a worklist is not being used. As illustrated in the example of FIG. 6B, the workload manager 620 can be expanded, such as by user selection, dragging, clicking, etc. In a two-column, collapsed tab state such as that shown in FIG. 6B, limited, high priority content such as patient name, identifier (ID), modality, urgency, etc., can be shown via the workload manager 620.

Figure 6C:
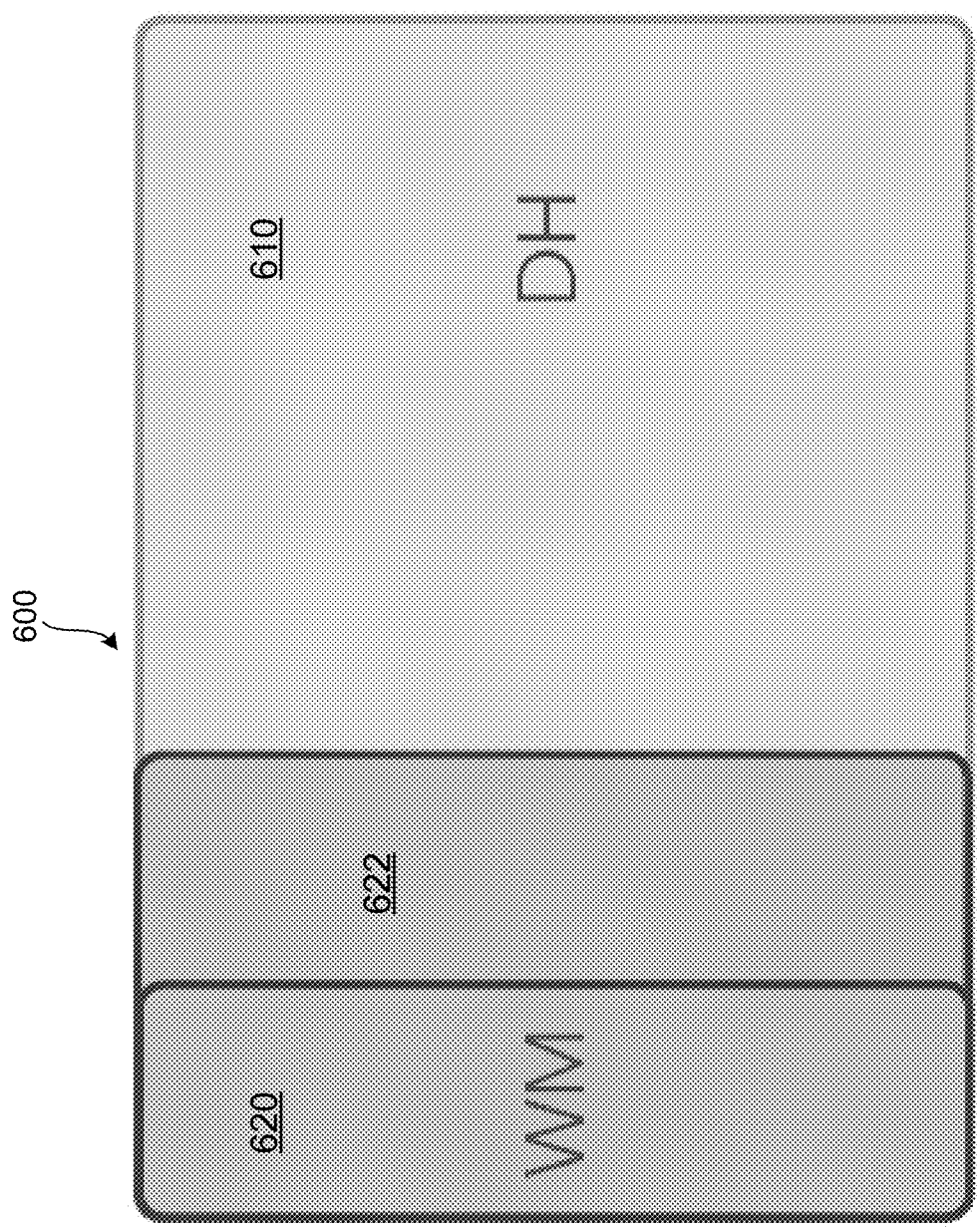

The example of FIG. 6C depicts an interface 600 in a three-column display state. In the example of FIG. 6C, the diagnostic hub 610 is shown in conjunction with a two-column workload manager 620, 622. The interface 600 of FIG. 6C provides a flexible user interface that responds to user selection. Content thresholds can be set to reveal appropriate levels of information depending on column 610, 620, 622 width.

Figure 6D:
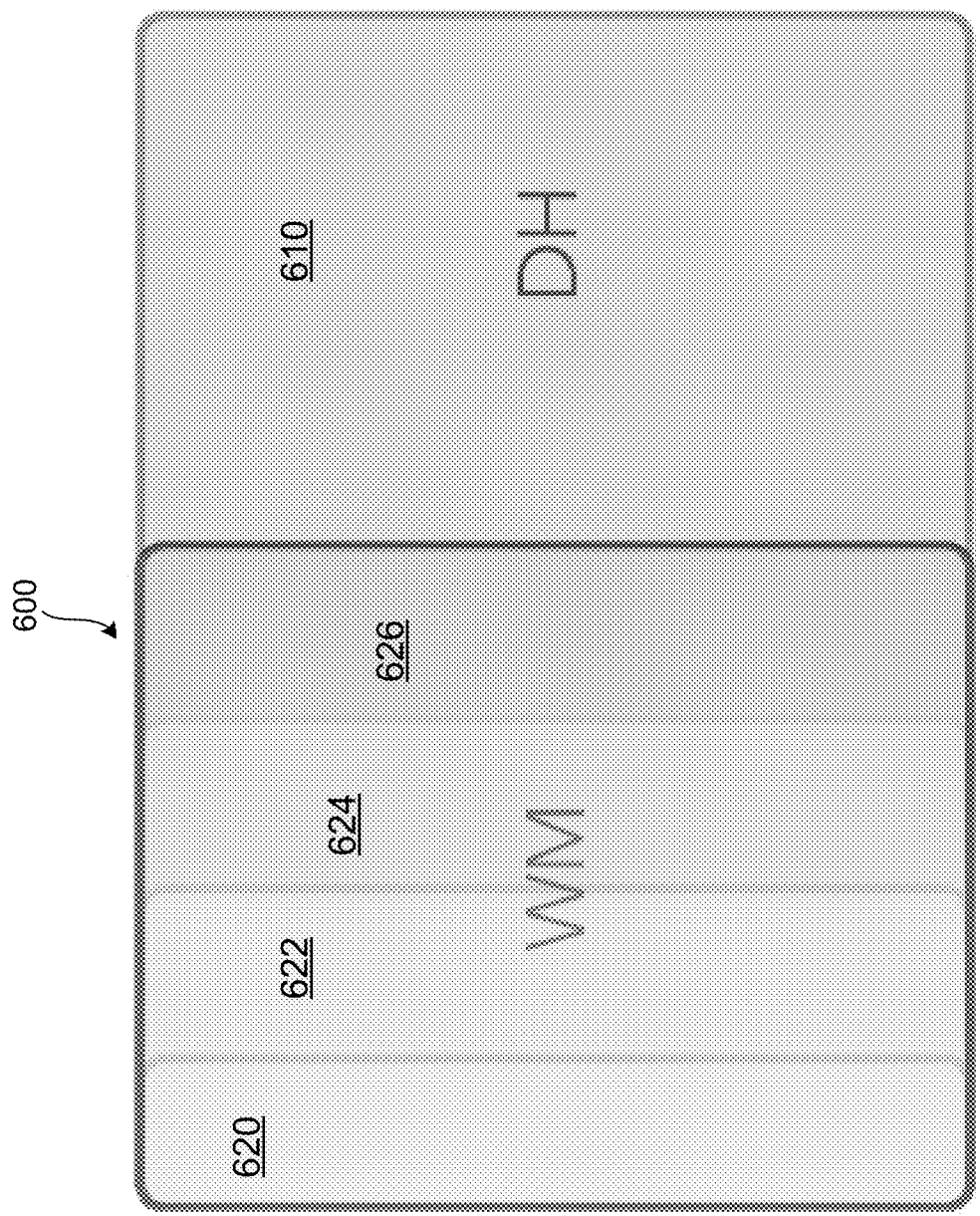

FIG. 6D provides another example in which the workload manager is divided according to a gradient into multiple columns 620, 622, 624, 626 in conjunction with the diagnostic hub 610. The example interface 600 of FIG. 6D also provides a flexible user interface that responds to user selection. Content thresholds can be set to reveal appropriate levels of information depending on column 610, 620, 622, 624, 626 width.

Figure 7:
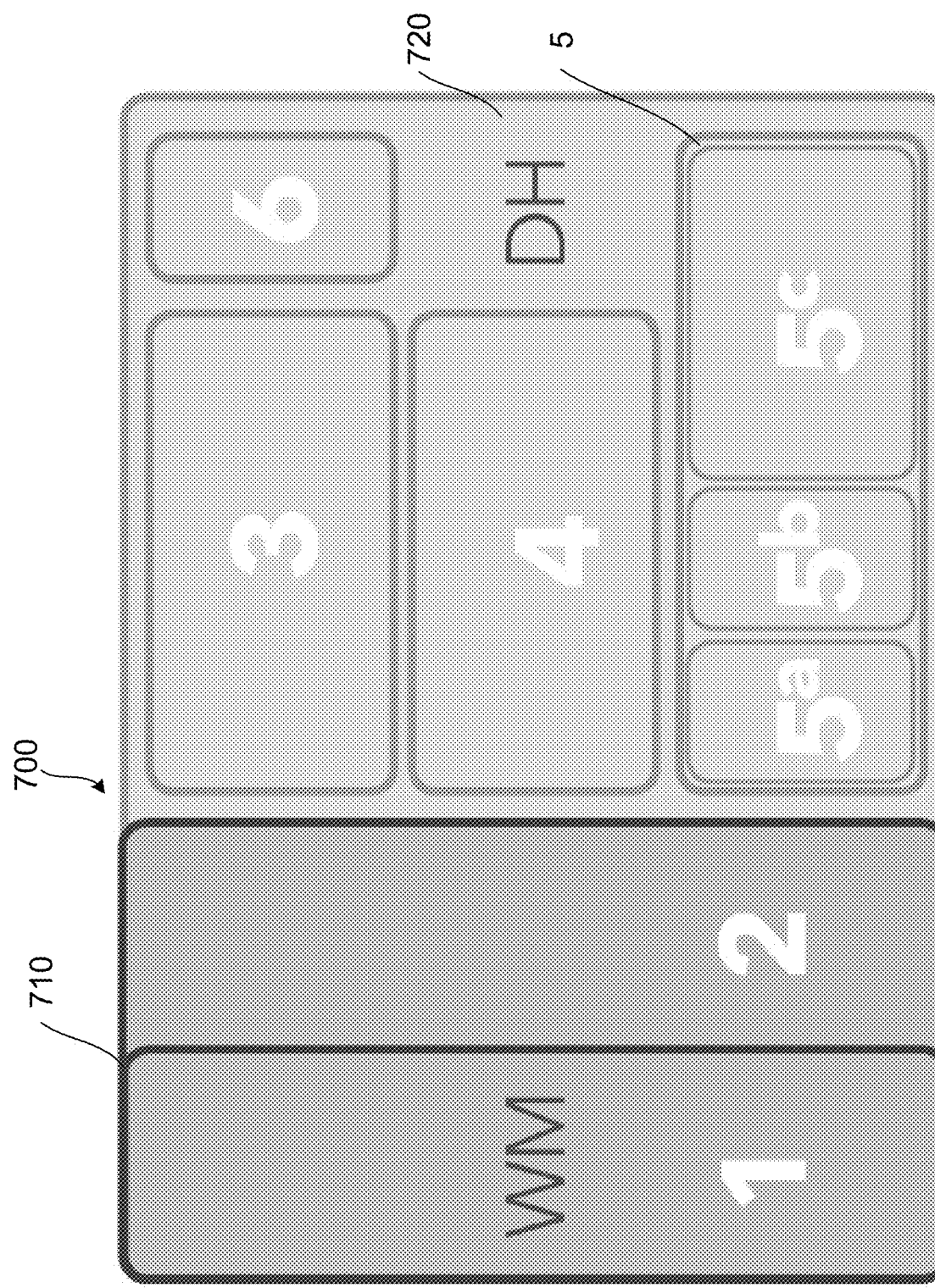
FIG. 7 illustrates an example radiology interface including a workload manager and a diagnostic hub.

FIG. 7 illustrates an example radiology interface 700 including a workload manager 710 and a diagnostic hub 720. The workload manager 710 shown in the example interface 700 includes a plurality of workload manager columns 1, 2. A first column 1 includes worklist tabs providing access to various tasks that a radiologist may address during a shift. A first category, 'My Work', houses various worklists from which a radiologist may choose to work. My Work can be divided into two subcategories: 1) items, potentially from any worklist, that a radiologist has actively reserved, been assigned by others to or begun reading ('Reserved,' 'Assigned', 'Saved Drafts', etc.), and 2) saved worklists that may be collaborative, cross-departmental, rotation-specific, and/or otherwise customized, for example. Other categories include 'Saved Cases', for cases that a radiologist wants to reference later, 'Messages' for communication and collaboration, 'My History' for easy access recently finalized exams, and 'Protocols' for scheduled or ordered exams that may involve consultation with a radiologist on proper exam performance, for example.

A second column 2 of the workload manager 710 provides an active worklist. When a radiologist selects a worklist, exams within the worklist are displayed in tile format in the second column 2 of the workload manager 710. Each tile includes metadata that can be useful when a radiologist is determining whether or not he/she is responsible for reading an exam (e.g., the metadata includes an indication of responsible/associated radiologist, patient, exam, referring physician, type, facility, etc.). If necessary or desired, a user can expand a width of the worklist to reveal more patient and exam metadata in each tile.

Several actions can be taken within and/or with respect to a worklist item. Each tile shows a status and available action(s) for the user (e.g., reserve, unreserve, assign, unassign, decline, accept, etc.). In some examples, a right click and/or other selection displays indication(s) of activity by other users on that exam (e.g., viewing, actively dictating, adding images, etc.). Stat or urgent cases can be marked with a red banner at the top left, for example. An exam can be selected from the worklist 4 and provided to the diagnostic hub 720.

The diagnostic hub 720 is a home for all of a patient's exam-related information (e.g., non-image data, etc.). The diagnostic hub 720 positions a radiologist to provide more accurate diagnoses by quickly highlighting relevant comparisons as well as a current patient's broader clinical history. For example, one or more related imaging studies, prior exams, patient history, and/or other clinical documentation can be displayed together with the current exam and/or other clinical scenario under review. In certain examples, file(s) and/or area(s)/portion(s) of files that are relevant can be highlighted for analysis.

The diagnostic hub 720 includes a patient banner 3. As shown in the example of FIG. 7, the patient banner 3 extends across a top of the diagnostic hub 720. The patient banner 3 can otherwise be positioned within the diagnostic hub 720 as well. The patient banner 3 displays patient demographic data as well as other patient information that is persistent and true regardless of the specific exam (e.g., age, medical record number (MRN), cumulative radiation dose, etc.).

The diagnostic hub 720 also includes a primary exam preview panel 4. The primary exam preview panel 4 provides a summary of the exam that the radiologist is currently responsible for reading (e.g., the exam that was selected from the worklist 2). As shown in the example of FIG. 7, the preview panel 4 is positioned below the patient banner 3 to help keep the radiologist focused on a current task. However, the preview panel 4 can be otherwise positioned in the diagnostic hub 720. Exam description and reason for exam can be displayed to identify the exam, followed by metadata such as exam time, location, referrer, technologist, etc.

A patient library 5 is devoted to helping a radiologist focus on relevant comparison exams, as well as any additional clinical content to aid in diagnosis. The patient library 5 of the diagnostic hub 620 includes subsection such as a clinical journey 5a, comparison list 5b, a comparison exam preview panel 5c, etc. The clinical journey 5a is a full patient 'timeline' of imaging exams, as well as other clinical data such as surgical and pathology reports, labs, medications, etc. The longitudinal view of the clinical journey 5a helps the radiologist notice broader clinical patterns more quickly, as well as understand a patient's broader context that may not be immediately evident in a provided reason for the primary exam. Tools can be provided to navigate within the clinical journey 5a. A user can adjust a time frame, filter for specific criteria, turn relevancy on or off, add or remove content categories, etc. The clinical journey 5a also integrates with the comparison list 5b. Modifying filter or search criteria in the clinical journey 5a can impact the exams displayed on the comparison list 5b.

The comparison list 5b is a vertical list of tiles, similar to the worklist 2, displaying available comparison exams for the current patient/primary exam. The comparison list 5b provides a quick access point for selecting comparisons, as opposed to the more longitudinal clinical journey 5a. Display can be limited to only show relevant exams by default, for example.

The comparison exam preview panel 5c is similar to the primary exam preview panel 4, with slight alterations in content display to account for a radiologist's shift in priorities when looking at a comparison (e.g., selected from the comparison list 5b, etc.). Rather than providing a reason for exam, a history and impression from the exam's report are displayed (or the whole report, if extraction is not possible or desired, etc.). The comparison previous panel 5c also generates and/or provides a relevancy score (e.g., 0-100%) based on body part, modality, exam time, and/or other variable(s), if available.

Figure 8:
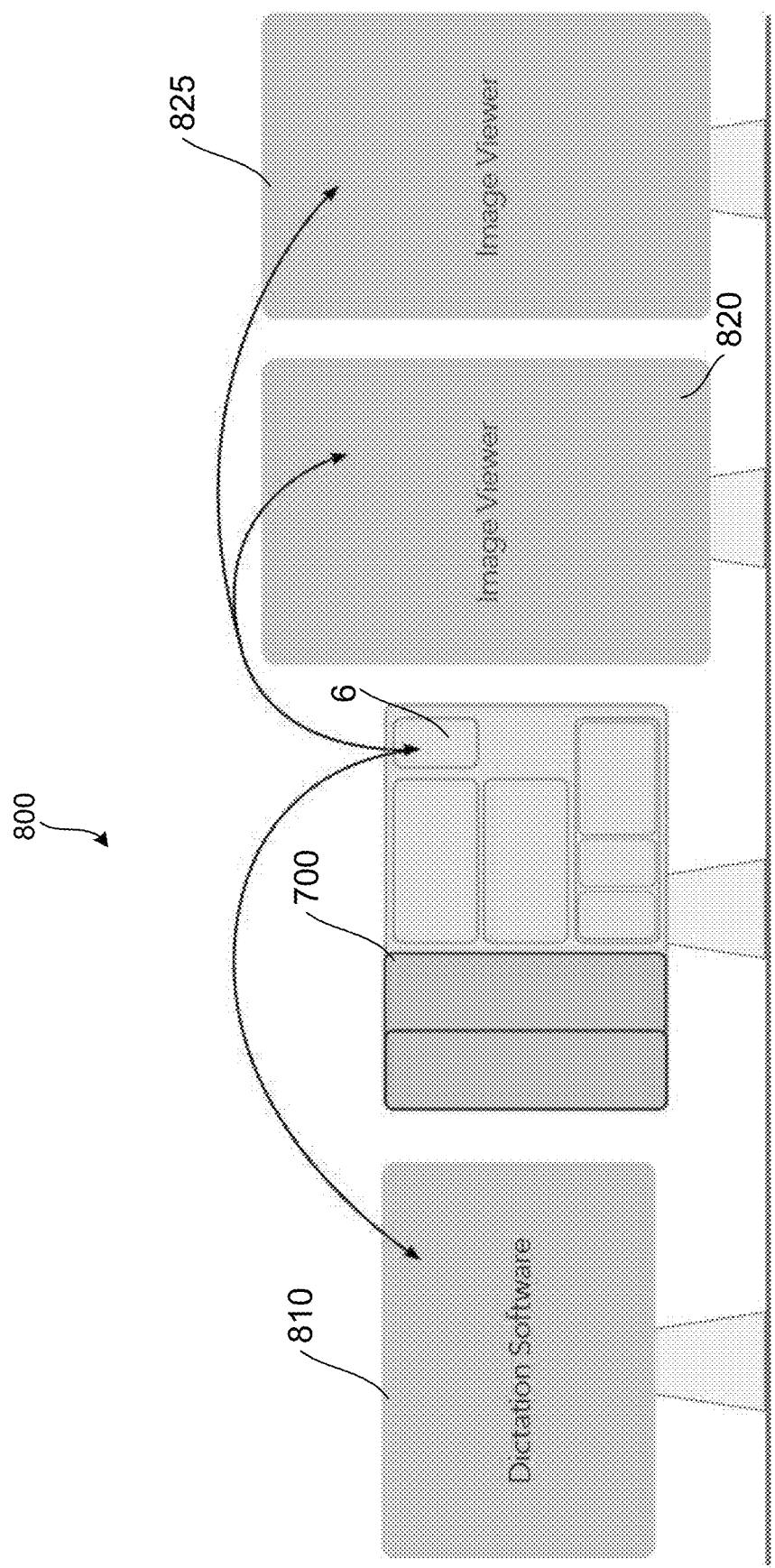
FIG. 8 illustrates an example system in which a bridge enables radiologists to easily navigate back and forth between a radiology desktop, image viewer(s), and dictation software, while maintaining patient context.

The diagnostic hub 720 can also include an image viewer/ dictation software bridge 6. As illustrated in the example of FIG. 8, the bridge 6 enables radiologists to easily navigate back and forth between the radiology desktop 700, image viewer 820, 825, and dictation software 810, while maintaining patient context. Using the bridge 6, a radiologist's complete end-to-end workflow can be supported.

Figure 9:
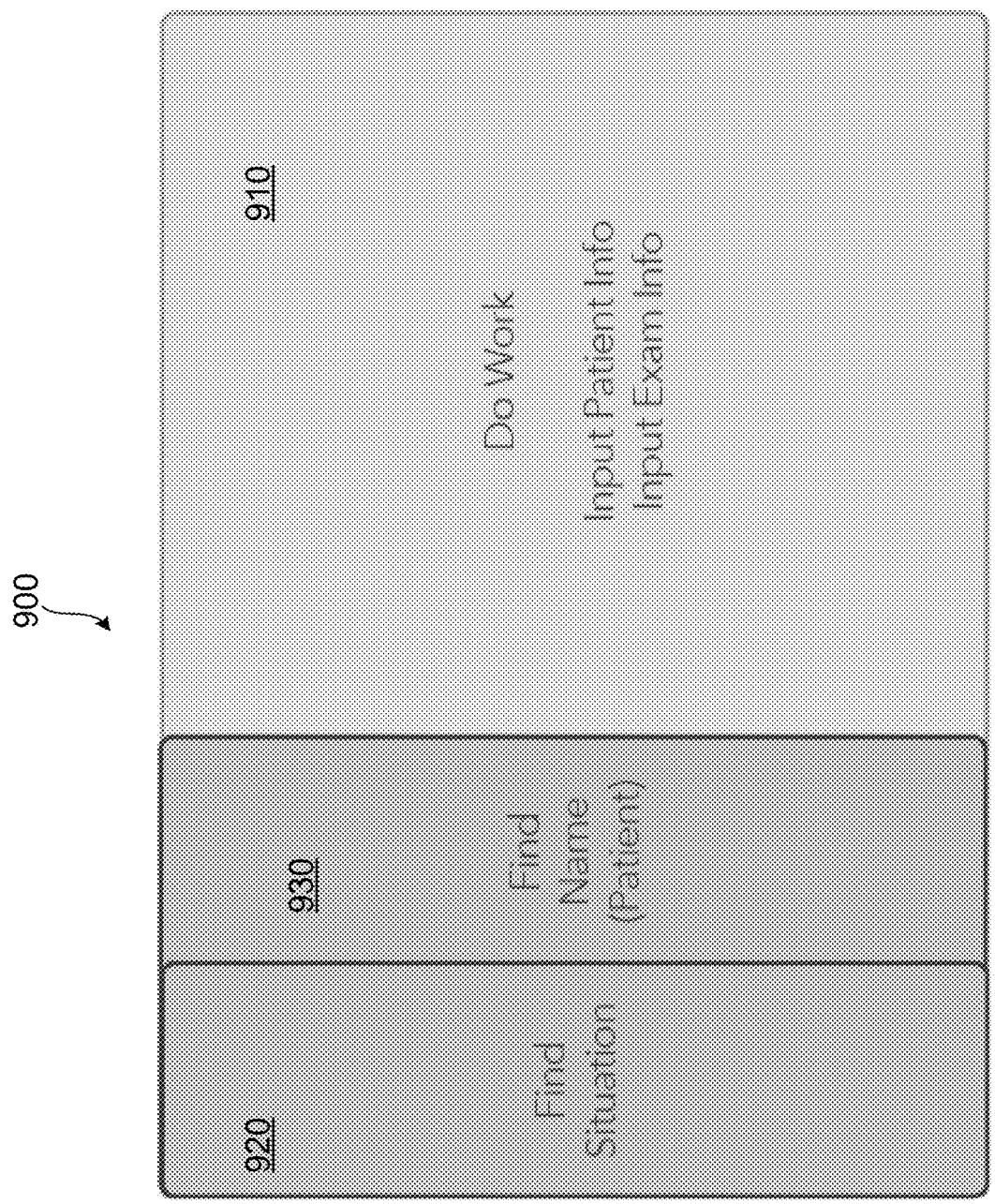
FIG. 9 illustrates an example technologist desktop.

In certain examples, a left-to-right, drill down model can be applied to roles other than a radiologist (other -ologies than radiology). FIG. 9 illustrates an example technologist desktop 900. The example technologist desktop interface 900 includes a work area 910 to input patient and exam information. The example interface 900 also includes a clinical situation finder 920 and a patient finder 930. Similar to the workflow described above, a user can search for a clinical situation via the situation finder 920, search for a name related to the situation via the name or patient finder 930, and work with respect to the identified patient and clinical situation via workspace 910. At each stage, information associated with the selection is dynamically retrieved and/or updated from an external source (e.g., a clinical data server, etc.) and dynamically rendered via the interface 900. The configuration of the interfaced 900 unfolds or expands into multiple columns and/or other sections based on selected option(s) and retrieved information, for example.

IV. EXAMPLE INTERACTION FRAMEWORK METHODS

Figure 10:
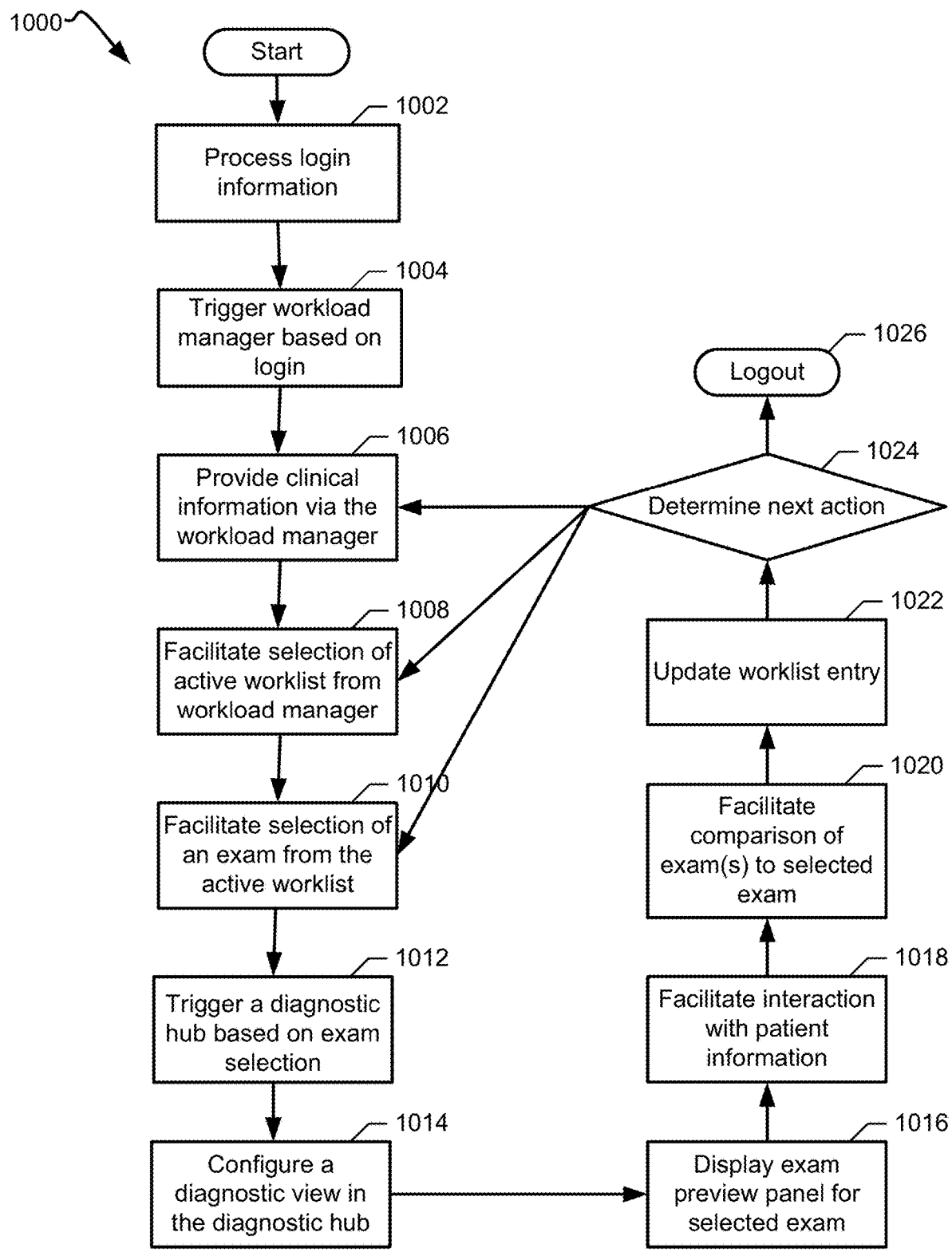
FIG. 10 illustrates a flow diagram for an example method to integrate a worklist with a diagnostic workspace via an interaction framework.

Flowcharts representative of example machine readable instructions for implementing and/or executing in conjunction with the example systems and interfaces of FIGS. 1-9 are shown in FIG. 10. In these examples, the machine readable instructions comprise a program for execution by a processor such as the processor 1112 shown in the example processor platform 1100 discussed below in connection with FIG. 11. The program can be embodied in software stored on a tangible computer readable storage medium such as a CD-ROM, a floppy disk, a hard drive, a digital versatile disk (DVD), a BLU-RAY™ disk, or a memory associated with the processor 1112, but the entire program and/or parts thereof could alternatively be executed by a device other than the processor 1112 and/or embodied in firmware or dedicated hardware. Further, although the example program is described with reference to the flowchart illustrated in FIG. 10, many other methods of implementing the examples disclosed and described here can alternatively be used. For example, the order of execution of the blocks can be changed, and/or some of the blocks described can be changed, eliminated, or combined.

As mentioned above, the example processes of FIG. 10 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 10 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 illustrates a flow diagram for an example method 1000 to integrate a worklist with a diagnostic workspace via an interaction framework. At block 1002, a login is processed to access the interaction framework. For example, a user provides information for single sign on (SSO) to a system including the interaction framework. At block 1004, based on the login, a workload manager (WM) is triggered. The WM is displayed via a graphical user interface on a display screen, for example. At block 1006, information, such as a plurality of worklists and perhaps a plurality of patients associated with the worklist(s), is provided via the WM.

At block 1008, selection of an active worklist from the WM is facilitated. The active worklist is displayed via the WM. At block 1010, selection of an exam from the active worklist is facilitated. For example, the active worklist displays a list of available exams associated with the active worklist, and one of the list of exams is selected.

At block 1012, a diagnostic hub (DH) is triggered based on selection of the exam. At block 1014, a diagnostic view is configured in the diagnostic hub for the selected exam according to the worklist and patient information. For example, the graphical user interface of the display screen adjusts the configuration such that the DH is displayed adjacent to the WM in the graphical user interface. A patient banner can be provided in conjunction with the selected exam via the DH diagnostic view. The patient banner provides certain summary, demographic, and/or other identifying information for a patient associated with the selected exam.

At block 1016, an exam preview panel is displayed based on the selected exam and patient. The exam preview panel provides a summary of the selected exam that the radiologist is currently responsible for reading, for example.

At block 1018, interaction with patient information is facilitated via the diagnostic view or workspace of the DH. Patient information can be viewed, reviewed, modified, added, deleted, etc., via the DH. At block 1020, one or more exams are chosen for comparison to the primary selected exam displayed via the preview panel. For example, a patient library provided via the DH provides relevant comparison exam(s) and/or other clinical content to aid in diagnosis.

At block 1022, a patient record and associated exam worklist entry can be updated based on the comparison. Thus, imaging-related clinical context, image review/comparison, and/or other clinical and/or operational insight can be factored into a report and/or other analysis of the exam. The report and/or other analysis can be saved in conjunction with the patient, exam, and/or worklist, for example.

At block 1024, after the update, a user can choose to branch to a variety of next actions. For example, control can switch to block 1006 with updated clinical information provided via the workload manager. Alternatively or in addition, control can shift to block 1008 for selection of another active worklist from the workload manager. As another option, control can shift to block 1010 for selection of another exam from the current active worklist. Alternatively, at block 1026, logout is facilitated.

Thus, via a graphical user interface can be configured to dynamically accommodate both a DH and WM and facilitate workload management as well as communication and collaboration among healthcare practitioners.

V. COMPUTING DEVICE

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 11:
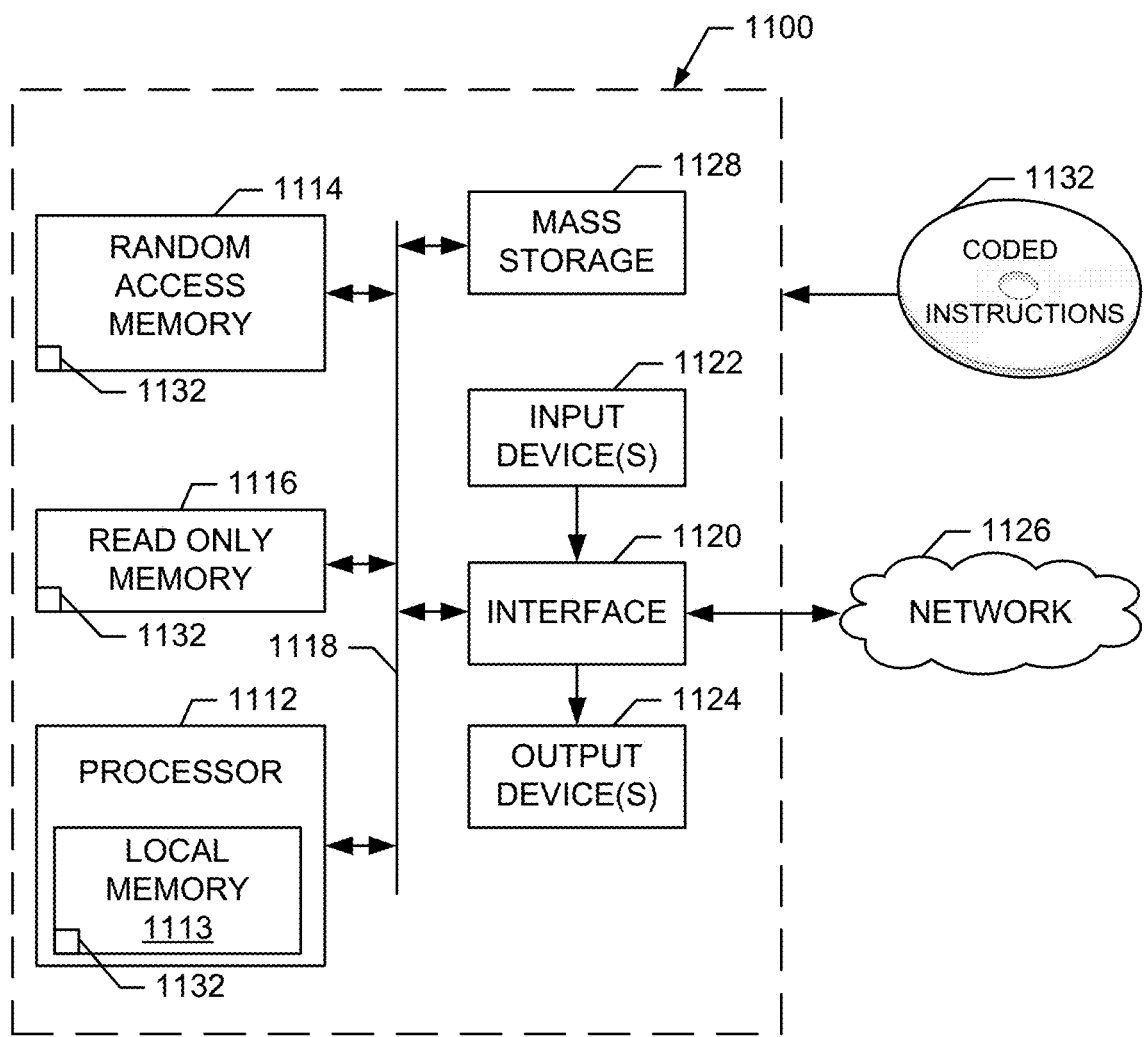
FIG. 11 shows a block diagram of an example processor system that can be used to implement systems and methods described herein.

FIG. 11 is a block diagram of an example processor platform 1100 capable of executing instructions to implement the example systems and methods disclosed and described herein. The processor platform 1100 can be, for example, a server, a personal computer, a mobile device (e.g., a cell phone, a smart phone, a tablet such as an IPAD™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors or controllers from any desired family or manufacturer.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 can be implemented by flash memory and/or any other desired type of memory device. Access to the main memory 1114, 1116 is controlled by a memory controller.

The processor platform 1100 of the illustrated example also includes an interface circuit 1120. The interface circuit 1120 can be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1120 of the illustrated example, thus, typically includes a graphics driver card, a graphics driver chip or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 can be stored in the mass storage device 1128, in the volatile memory 1114, in the non-volatile memory 1116, and/or on a removable tangible computer readable storage medium such as a CD or DVD.

VI. CONCLUSION

Thus, certain examples provide a diagnostic cockpit that aggregates clinical data and artifacts. Certain examples facilitate determination of data relevancy factoring in patient, user, and study context. Certain examples provide diagnostic decision support through the integrated diagnostic cockpit.

Certain examples provide general schema that can be ported to a variety of databases. Certain examples further provide a user-friendly wizard to create worklist definitions. Worklist definitions can be ported among schema. Certain examples leverage an entity framework to provide functionality, collaboration, modules, and metadata management in an entity framework, for example. Worklists can be dynamically build, and dynamically injected with context and user session information.

Certain examples provide a radiology desktop with a front end, a middle tier, and a back end. The front end provides a viewer, and the back end provides worklist data model(s), for example, The middle tier provides an application programming interface (API) along with business logic, data management, and data access. Business logic can include a worklist data processor and a reporting data processor, for example. Data manager can include adaptor(s), converter(s), data abstraction, cache, etc. Data access can include connector(s), access manager(s), query builder, etc.

Certain examples provide a dynamically adjustable interaction framework including both a workload manager and diagnostic hub accommodating a variety of worklists, exams, patients, comparisons, and outcomes. Certain examples improve operation of a graphical user interface and associated display and computer/processor through adaptive scalability, organization, and correlation.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost. Certain examples facilitate improved control over data. For example, certain example systems and methods enable care providers to access, view, manage, and manipulate a variety of data while streamlining workload management. Certain examples facilitate improved control over process. For example, certain example systems and methods provide improved visibility, control, flexibility, and management over workflow. Certain examples facilitate improved control over outcomes. For example, certain example systems and methods provide coordinated viewing, analysis, and reporting to drive more coordinated outcomes.

Certain examples leverage information technology infrastructure to standardize and centralize data across an organization. In certain examples, this includes accessing multiple systems from a single location, while allowing greater data consistency across the systems and users.

Technical effects of the subject matter described above can include, but are not limited to, providing systems and methods to enable an interaction and behavior framework for radiology and/or other healthcare technologies. Dynamic workflow and adaptive interface composition are driven based on available information, user preference, display configuration, etc. Moreover, the systems and methods of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of user interface management, the method comprising:
    triggering, based on a user identification in a user session, activation of a workload manager, the workload manager organizing and displaying, via a user interface on a display, one or more worklists associated with the user identification, the workload manager adjusting a configuration of the display to display the one or more worklists;
    retrieving and displaying, based on receiving a selection of an active worklist from the one or more worklists displayed via the workload manager in the user session, one or more exams associated with the active worklist, the workload manager adjusting the configuration of the display to display the active worklist and the one or more exams associated with the active worklist in the user session by dynamically modifying the user interface to add a plurality of columns to the user interface on the display upon activation of the workload manager, wherein a first column provides the one or more worklists for selection and wherein a second column provides the active worklist;
    triggering, based on selection of an exam from the one or more exams, activation of a diagnostic hub, the diagnostic hub and the workload manager displayed adjacently and operating concurrently while adaptively constructed in the user session based on an interaction with the user interface and a dynamic update from a server in communication with the user interface to change the user interface state, the diagnostic hub organizing and displaying, via the user interface on the display in the user session, a diagnostic view of information for the selected exam and a patient associated with the selected exam;
    generating, via the diagnostic hub, an exam preview panel providing a summary of the selected exam, the diagnostic hub adjusting the configuration of the display in the user session to display the exam preview panel in conjunction with the selected exam and the active worklist;
    facilitating comparison, based on selection of a comparison exam via the user interface from a patient library, between the selected exam and the comparison exam via the diagnostic hub, the diagnostic hub adjusting the configuration of the display in the user session for the comparison; and
    updating a worklist entry for the selected exam based on an analysis resulting from the comparison between the selected exam and the comparison exam in the user session.

2. The method of claim 1, further comprising generating, via the diagnostic hub, a patient banner providing a summary of a patient associated with the selected exam, the diagnostic hub adjusting the configuration of the display to display the patient banner in conjunction with the exam preview panel.

3. The method of claim 1, wherein the exam preview panel provides a summary of the selected exam.

4. The method of claim 1, further comprising enabling, via a bridge, navigation between the diagnostic hub, and image viewer, and dictation software while maintaining a patient context associated with the selected exam.

5. A radiology desktop system comprising:
    a processor configured to implement at least:
    a user interface to display information on a display;
    a workload manager to be triggered based on a user identification, the workload manager organizing and displaying, in a user session via the user interface on the display, one or more worklists associated with the user identification, the workload manager adjusting a configuration of the display in the user session to display the one or more worklists, wherein the workload manager retrieves and displays, based on receiving a selection of an active worklist in the user session from the one or more worklists displayed via the workload manager, one or more exams associated with the active worklist, the workload manager adjusting the configuration of the display in the user session to display the active worklist and the one or more exams associated with the active worklist by dynamically modifying the user interface in the user session to add a plurality of columns to the user interface on the display upon activation of the workload manager, wherein a first column provides the one or more worklists for selection and wherein a second column provides the active worklist; and a diagnostic hub triggered based on selection of an exam from the one or more exams in the user session, the diagnostic hub and the workload manager displayed adjacently and operating concurrently in the user session while adaptively constructed based on an interaction with the user interface and a dynamic update from a server in communication with the user interface to change the user interface state, the diagnostic hub organizing and displaying, in the user session via the user interface on the display, a diagnostic view of information for the selected exam and a patient associated with the selected exam, the diagnostic hub generating an exam preview panel providing a summary of the selected exam, the diagnostic hub adjusting the configuration of the display to display the exam preview panel in conjunction with the selected exam and the active worklist in the user session, wherein the diagnostic hub facilitates comparison, based on selection of a comparison exam via the user interface from a patient library, between the selected exam and the comparison exam via the diagnostic hub, the diagnostic hub adjusting the configuration of the display for the comparison in the user session, and wherein the diagnostic hub updates a worklist entry for the selected exam based on an analysis resulting from the comparison between the selected exam and the comparison exam.

6. The system of claim 5, wherein the diagnostic hub further generates a patient banner providing a summary of a patient associated with the selected exam, the diagnostic hub adjusting the configuration of the display to display the patient banner in conjunction with the exam preview panel.

7. The system of claim 5, wherein the exam preview panel provides a summary of the selected exam.

8. The system of claim 5, further comprising a bridge enabling navigation between the diagnostic hub, and image viewer, and dictation software while maintaining a patient context associated with the selected exam.

9. A non-transitory computer-readable storage medium including program instructions for execution by a computing device, the instructions, when executed, causing the computing device to implement at least:

a user interface displaying information on a display;

a workload manager to be triggered based on a user identification, the workload manager organizing and displaying, in a user session via the user interface on the display, one or more worklists associated with the user identification, the workload manager adjusting a configuration of the display in the user session to display the one or more worklists, wherein the workload manager retrieves and displays, based on receiving a selection of an active worklist in the user session from the one or more worklists displayed via the workload manager, one or more exams associated with the active worklist, the workload manager adjusting the configuration of the display in the user session to display the active worklist and the one or more exams associated with the active worklist by dynamically modifying the user interface in the user session to add a plurality of columns to the user interface on the display upon activation of the workload manager, wherein a first column provides the one or more worklists for selection and wherein a second column provides the active worklist; and a diagnostic hub triggered based on selection of an exam from the one or more exams in the user session, the diagnostic hub and the workload manager displayed adjacently and operating concurrently in the user session while adaptively constructed based on an interaction with the user interface and a dynamic update from a server in communication with the user interface to change the user interface state, the diagnostic hub organizing and displaying, in the user session via the user interface on the display, a diagnostic view of information for the selected exam and a patient associated with the selected exam, the diagnostic hub generating an exam preview panel providing a summary of the selected exam, the diagnostic hub adjusting the configuration of the display to display the exam preview panel in conjunction with the selected exam and the active worklist in the user session, wherein the diagnostic hub facilitates comparison, based on selection of a comparison exam via the user interface from a patient library, between the selected exam and the comparison exam via the diagnostic hub, the diagnostic hub adjusting the configuration of the display for the comparison in the user session, and wherein the diagnostic hub updates a worklist entry for the selected exam based on an analysis resulting from the comparison between the selected exam and the comparison exam.

10. The computer-readable storage medium of claim 9, wherein the diagnostic hub further generates a patient banner providing a summary of a patient associated with the selected exam, the diagnostic hub adjusting the configuration of the display to display the patient banner in conjunction with the exam preview panel.

11. The computer-readable storage medium of claim 9, further comprising a bridge enabling navigation between the diagnostic hub, and image viewer, and dictation software while maintaining a patient context associated with the selected exam.

12. The computer-readable storage medium of claim 9, wherein the workload manager divides worklist information among the plurality of columns according to one or more content thresholds.

13. The computer-readable storage medium of claim 9, wherein the diagnostic hub further includes a patient journey adjustable to modify a time frame and filter for the diagnostic hub and comparison exam from the patient library.

14. The method of claim 1, wherein the workload manager divides worklist information among the plurality of columns according to one or more content thresholds.

15. The method of claim 1, wherein the diagnostic hub further includes a patient journey adjustable to modify a time frame and filter for the diagnostic hub and comparison exam from the patient library.

16. The system of claim 5, wherein the workload manager divides worklist information among the plurality of columns according to one or more content thresholds.

17. The system of claim 5, wherein the diagnostic hub further includes a patient journey adjustable to modify a time frame and filter for the diagnostic hub and comparison exam from the patient library.

* * * * *